United States Patent [19]

Hadley et al.

[11] Patent Number: 5,731,408
[45] Date of Patent: Mar. 24, 1998

[54] PEPTIDES HAVING POTENT ANTAGONIST AND AGONIST BIOACTIVITIES AT MELANOCORTIN RECEPTORS

[75] Inventors: Mac E. Hadley; Victor J. Hruby, both of Tucson, Ariz.; Shubh D. Sharma, Albuquerque, N. Mex.

[73] Assignee: Arizona Board of Regents on behalf of the University of Arizona, Tucson, Ariz.

[21] Appl. No.: 420,972

[22] Filed: Apr. 10, 1995

[51] Int. Cl.$^6$ ........................................ C07K 7/00
[52] U.S. Cl. ........................ 530/317; 530/312; 930/270
[58] Field of Search ........................ 530/317, 312; 930/270

[56] References Cited

FOREIGN PATENT DOCUMENTS 9422460  10/1994  WIPO .

OTHER PUBLICATIONS

Adan et al., "Identification of antagonists for melanocortin MC$_3$, MC$_4$, and MC$_5$ receptors." *Eur. J. Pharmacol.*, 269, 331–338, 1994.

Johnson et al., "Coat color darkening in a dog in response to a potent melanotropic peptide." *Am. J. Vet. Res.*,55(11), 1593–6, 1994.

Ito et al., "Structure–Activity Correlations of Melanotropin Peptides in Model Lipids by Tryptophan Fluorescence Studies". *Biochemistry*, 32(45), 12264–72, 1993.

Primary Examiner—Cecilia J. Tsang
Assistant Examiner—C. Delacroix-Muirheid
Attorney, Agent, or Firm—Yahwak & Assoc.

[57] ABSTRACT

Cyclic lactam peptides, seven amino acids in length, having D-2'-naphthylalanine (D-2'-Nal) or D-para-iodo-phenylalanine D-(p-I)Phe at position 4 of the peptide provided potent and specific antagonists of the two neural melanocortin receptors and of the peripheral receptor. In particular, the peptide

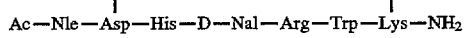

was found to be a potent antagonist of the MC3 and MC4 receptors with partial agonist activity, and a full agonist of the MC1 and MC5 receptors; the peptide

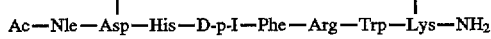

was found to be a potent antagonist of the MC3 and MC4 receptors with partial agonist activity. Both peptides have antagonist activities in the classical frog skin bioassay for pigmentation at the MC1 receptor.

3 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 7 amino acids
        ( B ) TYPE:amino acid
        ( C ) STRANDEDNESS:single
        ( D ) TOPOLOGY:cyclic ( i i ) MOLECULE TYPE:peptide ( i x ) FEATURE:
        ( D ) OTHER INFORMATION: cyclic from position 2 to position 7;
            Xaa at position 1 is norleucine; Xaa at positon 4 is
            D-2'- naphthylalanine ( x i ) SEQUENCE DESCRIPTION: SEQ ID NO:1:

Xaa   Asp   His   Xaa   Arg   Trp   Lys
                             5

( 2 ) INFORMATION FOR SEQ ID NO:2:

( i ) SEQUENCE CHARACTERISTICS:
        ( A ) LENGTH: 7 amino acids
        ( B ) TYPE:amino acid
        ( C ) STRANDEDNESS:single
        ( D ) TOPOLOGY:cyclic ( i i ) MOLECULE TYPE:peptide ( i x ) FEATURE:
        ( D ) OTHER INFORMATION: cyclic from position 2 to position 7;
            Xaa at position 1 is norleucine; Xaa at positon 4 is
            D-para-iodo- phenylalanine ( x i ) SEQUENCE DESCRIPTION: SEQ ID NO:2:

Xaa   Asp   His   Xaa   Arg   Trp   Lys
                             5

( 2 ) INFORMATION FOR SEQ ID NO:3:

( i ) SEQUENCE CHARACTERISTICS:
        ( A ) LENGTH: 13 amino acids
        ( B ) TYPE:amino acid
        ( C ) STRANDEDNESS:single
        ( D ) TOPOLOGY:linear ( i i ) MOLECULE TYPE:peptide ( i x ) FEATURE:
        ( D ) OTHER INFORMATION: Xaa at position 4 is norleucine; Xaa
            at position 7 is D- phenylalan ( x i ) SEQUENCE DESCRIPTION: SEQ ID NO:3:

Ser   Tyr   Ser   Xaa   Glu   His   Xaa   Arg   Trp   Gly   Lys   Pro   Val
                            5                                  10

PEPTIDES HAVING POTENT ANTAGONIST AND AGONIST BIOACTIVITIES AT MELANOCORTIN RECEPTORS

Research that led to the making of the present invention was supported, in part, by funds from the United States Public Health Service. Accordingly, the United States Government has certain statutory rights to the invention described herein under 35 USC 200 et seq..

While pharmacological methods have been traditionally used to define receptor types and subtypes, receptor cloning experiments have often led to the discovery of novel receptor types and subtypes within many receptor families. Following the cloning of the melanocyte stimulating hormone (MSH) gene [see Science 257:543 (1992)] and the adrenocorticotropic hormone (ACTH) receptor gene [see FEBS Lett. 309:417 (1992)], for example, three unique yet related genes were identified that also encoded functional, high affinity receptors for the MSH and ACTH peptides [see PNAS USA 90:8856 (1993); J. Biol. Chem. 268:8246 (1993); J. Biol. Chem. 268:15174 (1993); Biochem. Biophys. Res. Comm. 200:1214 (1994); Biochem. Biophys. Res. Comm. 195:866 (1993); Biochem. J. 299:367 (1994); Biochem. 33:4543 (1994); Mol. Endo. 8:1298 (1994); J. Mol. Endochrinol. 12:203 (1994); and Biochem. Biophys. Res. Comm. 200:1007 (1994)]. Named by number in the order of their discovery, the melanocortin-3, melanocortin-4, and melanocortin-5 receptor genes have been found thus far to be expressed primarily in the hypothalamus, mid-brain and brainstem (MC3-R, and MC4-R), or in a wide distribution of peripheral tissues (MC5-R).

The melanocortin peptides have been reported to have a wide variety of biological activities outside of their effects upon pigmentation and steroidogenesis, known to be mediated by the MSH and ACTH receptors. However, given the complexity of possible sites of expression of the MC3, MC4 and MC5 receptors, it has not been possible to unambiguously identify any simple correlation between these receptors and the reported biological activities of their ligands. Consequently, potent and specific agonists and antagonists would be extremely valuable tools for determining the physiological roles of the MC3, MC4 and MC5 receptors; the roles of the MC1 (pigment cell receptor) and MC2 (primary receptor for ACTH in the adrenal gland) receptors are fairly well-documented.

While prior structure-function analyses have been reported in the past on the affinity and potency of the α-MSH peptide at the MSH receptor site [for reviews see Peptide Protein Rev. 3:1 (1984), The Melanotropic Peptides, Vol. I, II, and III (CRC Press) (1988)], only a few relatively weak antagonists have resulted from these studies [see Int. J. Peptide Protein Res. 35:228 (1990); Peptides 11:351 (1990); and Peptide Res 3:140 (1989)].

Accordingly there is still a need to provide for potent and specific antagonists that will allow for the determination of the physiological roles of the MC3, MC4 and MC5 receptors.

It is, therefore, a primary aspect of the present invention to describe the discovery of melanocortin analogues that are potent and selective antagonists of the MC1, MC3 and MC4 receptors.

More specifically, the present description describes two potent antagonists for the MC1, MC3 and MC4 receptors that are heptapeptides having the cyclic peptide structures:

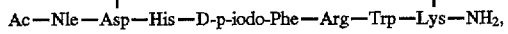

and

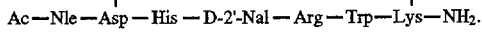

This and other aspects of the present invention will become clearer in the following discussion and description, both provided for purposes of clarification and not limitation as to the scope of the present invention.

In the following description, the abbreviations used for amino acids, protecting groups and peptides follow the recommendations of the IUPAC-IUB Commission on Biochemical Nomenclature as described in J. Biol. Chem. 250:3215 (1975); all optically active amino acids are of the L variety unless otherwise specified (since each of the peptides described herein contain at least one D amino acid, the resulting peptides are considered to be D-amino acid-containing peptides). Other abbreviations include Nle indicating norleucine, OFm indicating fluorenylmethyloxy, Fmoc indicating fluorenylmethyloxycarbonyl, MC indicating melanocortin; and MC-R indicating melanocortin receptor.

EXAMPLE I

The peptide

was synthesized by solid-phase methods of peptide synthesis [see J. Med. Chem. 30:2126 (1987)] on a p-methylbenzhydrylamine resin (substitution 0.34 meq amine/g resin) using a VEGA 250 semi-automated peptide synthesizer. A four-fold excess of appropriate $N^\alpha$-Boc protected amino acid was used at each coupling step. Couplings were performed by using diisopropylcarbodiimide-N hydroxybenzotriazole (DIC-HOBt) as coupling reagent, and were monitored by the Kaiser test [see Anal. Biochem. 34:595 (1970)] in all cases. A mixture of trifluoroacetic acid-dichloromethane-anisole (TFA-DCM-anisole, 50:48:2) was used to deblock the $N^\alpha$-Boc group after each coupling step. Neutralization was accomplished using diisopropylethylamine in dichloromethane. In this manner, the following fully protected peptide-resin corresponding to the titled peptide was synthesized: $N^\alpha$-Boc-Asp(OFm)-His(Bom)-D-(P-I)Phe-Arg(Tos)-Trp-Lys(Fmoc)-Resin. The $N^{68}$ -Fmoc group from Lys and the β-OFm from Asp were cleaved simultaneously by the treatment of the peptide-resin with 20% piperidine in N-methyl pyrrolidone (NMP) for 20 minutes. The resulting ε-$NH_2$ and β-COOH side chain functional groups in the peptide resin $N^\alpha$-Boc-Asp-His (Bom)-D-(p-I)Phe-Arg(Tos)-Trp-Lys-Resin were condensed together using benzotrizole-1-yl-oxy-tris-(dimethylamino)-phosphonium hexafluorophosphate (BOP) reagent (at a 4-fold molar excess) in NMP in the presence of a 5-fold molar excess of diisopropylethylamine (DIEA) as described previously in the literature [see J. Med. Chem. 32:2555 (1989)]. The coupling as monitored by the Kaiser test was completed in 2.5 hours. The $N^\alpha$-Boc group was cleaved, and $N^\alpha$-Boc-Nle was coupled to the N-terminus using DCI-HOBt methodology.

After removal of the $N^\alpha$-Boc group, the N-terminus amino group was acetylated. The dried peptide resin was treated with HF-anisole for 45 minutes at 0° C., and the resulting crude peptide purified by HPLC and characterized by fast atom bombardment mass spectrometry and amino acid analysis. Analytical HPLC was performed on a C-18 column (Vydac 218TP104, 25 cm×4.6 mm). Thin layer chromatography (TLC) was performed on Baker 250-nm analytical silica gel glass plates in the following solvent systems: (A) 1-butanol/acetic acid/pyridine/water (5:1:5:4 v/v); (B) 1-butanol/acetic acid/pyridine/water (15:3:10:12 v/v); (C) 1-butanol/acetic acid/water (4:1:5). The peptides were visualized by ninhydrin and iodine vapor.

The analytical data for the peptide is: Mass 1151 (calc. 1150.09) via fast atom bombardment mass spectrometry; $[\alpha]D^{23} = -45.4°$ (c, 0.05, 10% aq. AcOH); HPLC K'=6.83 (gradient of 20% to 40% acetonitrile in 0.1% aq. TFA completed in 30 minutes at 1.5 ml/min); TLC $R_f$ values=0.84 (1- butanol/HOAc/pyridine/$H_2O$, 5:1:5:4 solvent system), 0.02 (EtOAc/pyridine(HOAc/$H_2O$, 5:5:1:3 solvent system), 0.68 (1-butanol/HOAc/$H_2O$, 4:1:5 solvent system).

EXAMPLE II

The peptide

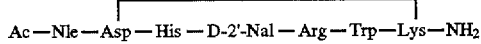

Ac—Nle—Asp—His—D-2'-Nal—Arg—Trp—Lys—$NH_2$ was synthesized by solid-phase methods of peptide synthesis in a similar manner to that described in Example I. Briefly, the synthesis was accomplished on a p-methylbenzhydrylamine-resin using an Na-Boc strategy that included cyclization of the lactam bridge on the solid support by the use of benzotrizole-1-yl-oxy-tris-(dimethylamino)-phosphonium hexafluorophosphate (BOP) reagent (at a 4-fold molar excess) in NMP in the presence of a 5-fold molar excess of diisopropylethylamine (DIEA) as described previously in the literature [see J. Med. Chem. 32:2555 (1989)]. Side chain protection was achieved by use of Asp(OFm), His(Born), Arg(Tos), and Lys(Fmoc). The cyclic, partially protected peptide was cleaved from the Resin and the remaining side chain groups removed by treatment with HF-anisole for 45 minutes at 0° C. The resulting crude peptide was purified by reverse phase HPLC and characterized by analytical RP-HPLC and by thin layer chromatography on silica gel plates in three different solvent systems as described above.

The analytical data for the peptide is: Mass spectra: 1075 (calc. 1075.3) via fast atom bombardment mass spectrometry; $\alpha^{22}589 = -65.2°$ (c, 0.018, 10% aq. AcOH); HPLC K'=7.28 (gradient of 20% to 40% acetonitrile in 0.1% aq. TFA completed in 30 minutes at 1.5 ml/min); TLC $R_f$ values=0.79 (1-butanol/HOAc/pyridine/$H_2O$, 5:1:5:4 solvent system), 0.01 (EtOAc/pyridine(HOAc/$H_2O$, 5:5:1:3 solvent system), 0.65 (1-butanol/HOAc/$H_2O$, 4:1:5 solvent system).

EXAMPLE III

Bioassays were performed on frog (*Rana pipiens*) and lizard (*Anolis carolinensis*) skins according to published protocols [see J. Med. Chem. 30:2126 (1987) and Gen. Comp. Endocrinol. 55:104 (1984)]. Briefly, in these assays the darkening of skin due to dispersion of melanin granules within the melanocytes in response to the melanotropin peptides according to the present invention is measured by photoreflectance methods. The agonist potency of each peptide was determined from the dose response curves comparing the skin darkening with that produced by the native hormone, α-MSH. Prolongation of the biological response was measured by continued monitoring of the melanosome dispersion for up to 3 hours following removal of the peptide in the bathing solution through washing of the skins. The antagonistic activity profile was measured by pre-incubating the skins for 1 hour in various concentrations of the antagonist. After pre-incubation, a known concentration of α-MSH was added and its melanotropic activity determined. Dose-response curves generated for α-MSH in this manner were used to determine the $pA_2$ values (representing the $-\log10$ of the average molar concentration of the antagonist that will reduce the response of α-MSH (agonist) from 2X units to X units) [see Br. J. Pharmacol. 2:189 (1947)].

In addition to the classical frog and lizard skin assays conducted in accordance with this example, additional assays for agonist and antagonistic activity were performed.

EXAMPLE IV

The peptides according to the present invention were assayed for agonist and antagonist activity using cloned hMC1, mMC1-R, hMC3-R, hMC4-R and mMC5-R transfected into the stable cell line Clonal 293. Transduction was measured by its affect on cAMP production using the following method.

Clonal 293 cell lines expressing the human MSH receptor, human MC3-R, human MC4-R, and mouse MC5-R were transfected with a pCRE/β-galactosidase construct using a $CaPO_4$ method [see Mol. Cell. Biol. 7:2745 (1987)]. 4 μg of pCRE/β-galactosidase DNA was used for transfection of a 10 cm dish of cells. After 15 to 24 hours post-transfection, cells were split into 96-well plates with 20,000 to 30,000 cells per well, and incubated at 37° C. in a 5% $CO_2$ incubator until 48 hours post-transfection. Cells were then stimulated with different peptides diluted in stimulation medium (Dulbecco's modified Eagle's medium containing 0.1 mg/ml bovine serum albumin and 0.1 mM isobutylmethylxanthine) for 6 hours. Agonist activity was measured by stimulating cells with various concentrations of peptide, and antagonist activity was measured by stimulating MC3 and MC4 receptor cell lines with various concentrations of peptide. After stimulation, cells were lysed in 50 μl lysis buffer (250 mM Tris-HCl, pH 8.0, 0.1% Triton X-100), frozen and thawed, and then assayed for b-galactosidase activity. The results are tabulated below:

TABLE 1

| Assay | Peptide | |
|---|---|---|
| | D-2'-naphthylalanine | D-para-iodo-phenylalanine |
| mMC5-R | | mixed agonist/antagonist |
| | ($EC_{50}$ = 434 ± 260 pM) | ($EC_{50}$ = 684 ± 260 pM) |
| hMCR4-R | antagonist | mixed agonist/antagonist |
| | ($pA_2$ = 9.3) | ($pA_2$ = 9.5) |
| | ($EC_{50}$ = no activity) | ($EC_{50}$ = 573 ± 357 pM) |
| hMC3-R | mixed agonist/antagonist | mixed agonist/antagonist |
| | ($pA_2$ = 8.3) | ($pA_2$ = 8) |
| | ($EC_{50}$ = 2813 ± 575 pM) | ($EC_{50}$ = 1134 ± 197 pM) |
| mMC1-R | full agonist | full agonist |
| | ($EC_{50}$ = 9 nM) | ($EC_{50}$ = 10 nM) |
| hMC1-R | full agonist | full agonist |
| | ($EC_{50}$ = 36 pM) | ($EC_{50}$ = 55 pM) |
| frog skin | antagonist | antagonist |
| | ($pA_2$ = >10.5) | ($pA_2$ = 10.3) |
| lizard skin | agonist | agonist |
| | | ($EC_{50}$ = 0.16 nM) |

As shown in Table I, the D-2'-Nal containing peptide according to the present invention has no agonist activity up to the 10⁶M level at the hMC4-R, and is a potent antagonist at this receptor with a pA₂ value of 10. At the hMC3-R, this significant alteration in IC50 values were observed relative to those calculated for Ac-[Nle⁴, D-Phe⁷]α-MSH.

TABLE II

| peptide | receptor | |
|---|---|---|
| | hMC3R | hMC4R |
| Ac-[Nle⁴, D-Phe⁷]α-MSH | 3.8 | 3.6 |
| Ac—Nle—Asp—His-p-I—D—Phe—Arg—Trp—Lys—NH₂ | 1.8 | 2.5 |
| Ac—Nle—Asp—His—D-2'-NaI—Arg—Trp—Lys—NH₂ | 3.3 | 1.8 | peptide is a partial agonist that can only partially stimulate (about 20% that of α-MSH) the cAMP response. However, it also has potent partial antagonist activity (pA₂=10.3). On the other hand, at the cloned hMC1-R and mMC1-R, this peptide is a potent agonist that is about equipotent to α-MSH with only very weak partial antagonist activity. In the frog skin bioassay, the peptide is a potent antagonist, and in the lizard skin bioassay this peptide is a full agonist. As used in the above table, EC₅₀ is the effective concentration necessary for 50% of maximal activity.

The D-p-iodo-Phe containing peptide according to the present invention has virtually no agonist activity in the frog skin assay, but is a potent antagonist with a pA₂ of 10.3. However, in the lizard skin bioassay, this peptide is a potent full agonist that is about 1.7-fold more potent than α-MSH. in the cloned receptor bioassays, the peptide is a full agonist at the MC1 receptor in agreement with the lizard skin bioassay system, but in contrast to the frog skin bioassay system. Moreover at the MC4-R and MC3-R receptors, the peptide is a mixed agonist/antagonist with fairly potent antagonist activity.

Competition binding experiments were also performed to determine if iodination of the phenylalanine aromatic ring or replacement of the phenyl ring with a naphthyl ring had any effect on the affinity of the cyclic lactam compounds for the MC3 or MC4 receptors according to the following example:

EXAMPLE VI

Cell lines expressing the hMC3-R or hMC4-R were plated at 1×10⁶ cells/well in 24-well plates. Prewarmed PBS-BSA solution (1 mg/ml BSA in PBS solution) containing 3.1× 10⁻¹⁰M I¹²⁵-Ac-[Nle⁴, D-Phe⁷]α-MSH (100,000 cpm) and different concentrations of Ac-[Nle⁴, D-Phe⁷]α-MSH,

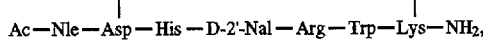

or

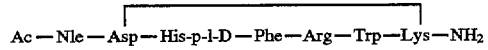

was added to each well. Cells were incubated for 30 min at 37° C. in a 5% CO₂ incubator, washed twice with PBS-BSA at 37° C., lysed with 500 μl 0.5N NaOH, and counted with a γ counter. Nonspecific binding, determined as the amount of radioactivity bound at 5×10–6M cold Ac-[Nle⁴, D-Phe⁷] α-MSH, was 3–5% of the total counts bound.

The data from these series of experiments is reported in the following Table II. In this series of experiments, no A number of peptides similar in structure to that of the peptides described in Examples I and II were prepared and tested for potential antagonist activity for the MC3 and MC4 receptors. The following table provides a summary of the status for a number of these peptides and clearly indicates the specificity of antagonist activity to limited chemical structures (a structure-activity relationship). In this table, all peptides shown are cyclic lactam compounds that have the generalized amino acid sequence

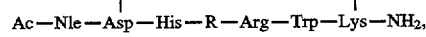

wherein R represents the D-amino acid residue as indicated.

TABLE III

| Peptide | status |
|---|---|
| D-Phe | Agonist |
| D-homoPhe | Agonist |
| D-(p-F)Phe | Agonist |
| D-(p-Cl)Phe | Agonist |
| D-(p-I)Phe | Antagonist |
| D-Tyr | Agonist |
| D-(3',5'-di-I)Tyr | Agonist |
| D-(p-nitro)Phe | Agonist |
| D-(naphthylalanine) (D-2'-Nal) | Antagonist |

In addition to the property of the peptides according to the present invention as potent and specific agonists and antagonists, thereby making them an extremely valuable research tool for determining the physiological roles of the MC1, MC3, MC4 and MC5 receptors, these peptides may also be used to block the normal physiological response of cells to natural melanotropin (e.g., α-MSH). For example, some researchers have suggested that melanoma tumor cells secrete α-MSH which then results in a proliferation of these cells. If so, an antagonist such as the peptides according to the present invention might help delay melanoma growth and metastases; if a melanotropin is known to cause a physical or biochemical response in man, an antagonist may block such a response. Considering the present level of understanding on both peripheral and CNS receptors, some of the potential uses of the antagonists according to the present invention might be to block the proposed autocrine and/or paracrine actions of α-MSH in the proliferation of melanoma tumors; as a vector to direct therapeutic ligands at the site of specific classes of MSH receptors; and the structural features of the peptides according to the present invention suggest that they may have facile passage across the blood-brain barrier and as such these antagonists may find extensive uses as intervention agents in various physiological processes mediated in the brain or in the periphery by MSH such as, for example, learning and memory processes, sexual behavior, regulation of body temperature, immune response, and as a vehicle for drugs that may otherwise not cross the blood-brain barrier. Unfortunately, until such uses of the peptides can be shown, they remain speculative.

A complete sequence listing for the peptides described in this specification is provided below:

Having thus described our invention and the manner and process of making and using it in such full, clear, concise and exact terms so as to enable any person skilled in the art to which it pertains, or with which it is most nearly connected, to make and use the same;

We claim:
1. A cyclic peptide selected from the group consisting of:
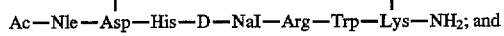
Ac—Nle—Asp—His—D—Nal—Arg—Trp—Lys—NH$_2$; and
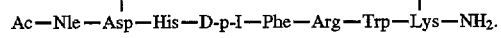
Ac—Nle—Asp—His—D-p-I—Phe—Arg—Trp—Lys—NH$_2$.
2. A peptide according to claim 1 which is:
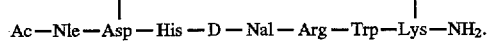
Ac—Nle—Asp—His—D—Nal—Arg—Trp—Lys—NH$_2$.
3. A peptide according to claim 1 which is:
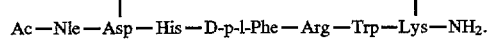
Ac—Nle—Asp—His—D-p-l-Phe—Arg—Trp—Lys—NH$_2$.
* * * * *